(12) United States Patent
Dey et al.

(10) Patent No.: US 8,372,653 B2
(45) Date of Patent: Feb. 12, 2013

(54) MASS TAG REAGENTS FOR SIMULTANEOUS QUANTITATION AND IDENTIFICATION OF SMALL MOLECULES

(75) Inventors: Subhakar Dey, N. Billerica, MA (US); Subhasish Purkayastha, Acton, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 107 days.

(21) Appl. No.: 13/011,960

(22) Filed: Jan. 24, 2011

(65) Prior Publication Data
US 2011/0183420 A1    Jul. 28, 2011

Related U.S. Application Data

(60) Provisional application No. 61/297,507, filed on Jan. 22, 2010.

(51) Int. Cl.
*G01N 24/00* (2006.01)
*B01D 59/44* (2006.01)

(52) U.S. Cl. .............. 436/173; 436/8; 436/56; 436/87; 436/161; 436/128; 250/281; 250/282

(58) Field of Classification Search ................ 436/8, 56, 436/86, 87, 161, 173, 174, 106, 119, 127, 436/128; 422/430, 70; 250/281, 282
See application file for complete search history.

(56) References Cited

U.S. PATENT DOCUMENTS

| | | | |
|---|---|---|---|
| 2005/0098719 A1* | 5/2005 | Thomson | 250/288 |
| 2006/0172319 A1* | 8/2006 | Yan et al. | 435/6 |
| 2008/0044857 A1* | 2/2008 | Anderson | 435/71.1 |
| 2008/0318327 A1* | 12/2008 | Bjellqvist et al. | 436/89 |
| 2011/0003395 A1* | 1/2011 | Dey et al. | 436/98 |
| 2011/0111513 A1* | 5/2011 | Baumann et al. | 436/89 |

* cited by examiner

*Primary Examiner* — Maureen Wallenhorst

(57) ABSTRACT

A molecule identification and quantitation method is provided wherein a mass tag is conjugated to an analyte and the signature ion of the mass tag remains attached to the analyte after tandem mass spectrometry fragmentation (MS-MS or $MS^2$). Rather than losing the signature ion, a mass-balance part of the structure can be lost as a charge neutral group under tandem mass spectrometry fragmentation. The signature ion can be used for quantitation and, upon further fragmentation, can also provide ion-signals characteristic of the analyte and useful in identifying the analyte. In some embodiments, the ion-signals generated from a third mass spectrometry fragmentation ($MS^3$) can be compared with a known mass spectrum, for example, from a look-up table, from a library, or from a database, to provide an unambiguous identification of the analyte.

13 Claims, 13 Drawing Sheets

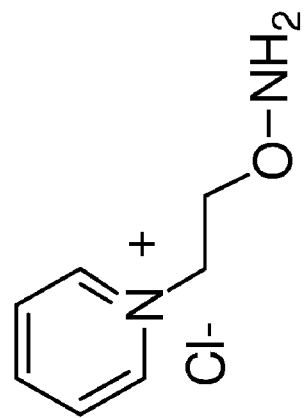
FIG. 2C
FIG. 2B
FIG. 2A
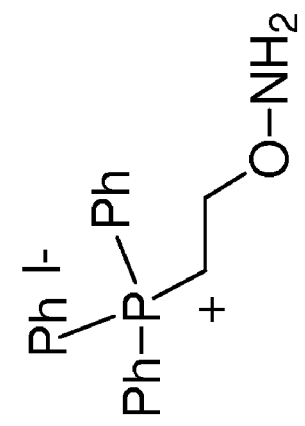
FIG. 2E
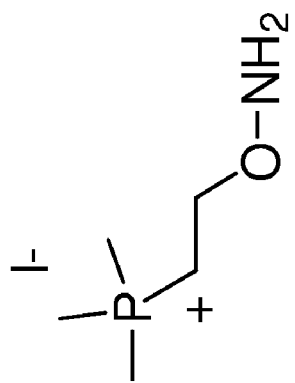
FIG. 2D

MASS TAG REAGENTS FOR SIMULTANEOUS QUANTITATION AND IDENTIFICATION OF SMALL MOLECULES

CROSS-REFERENCE TO RELATED APPLICATIONS

The present application claims benefit from earlier filed U.S. Provisional Patent Application No. 61/297,507, filed Jan. 22, 2010, which is incorporated herein in its entirety by reference.

FIELD

The present teachings relate to the field of mass spectrometry and detecting and quantifying small molecules

BACKGROUND

Tagged-analyte complexes are fragmented in a mass spectrometer to generate a charged signature ion. The signature ion is used to quantify the tagged analyte. Unfortunately, during the fragmentation process, positive charge is predominately transferred to the signature ion and the remaining charge-neutral portion of the molecule containing the analyte remains undetected or under-detected. Subsequent analysis for fragmentation of the charged neutral portion containing the analyte does not lead to unambiguous identification of the analyte. A need exists for a method for the simultaneous quantitation and identification of small molecules, for example, metabolites.

SUMMARY

According to various embodiments of the present teachings, a method of analyzing an analyte is provided that comprises both quantitating and identifying the analyte. The method can comprise covalently bonding a tag to the analyte to form a labeled analyte. The method can comprise subjecting the labeled analyte to a first step of mass spectrometry fragmentation under first conditions that do not dissociate the labeled analyte. In some embodiments, the method can then comprise subjecting the labeled analyte to a second step of mass spectrometry fragmentation (MS-MS or $MS^2$) under second conditions that differ from the first conditions. The second step of mass spectrometry fragmentation can cause the formation of a mass spectrum and the second conditions can comprise conditions that dissociate the labeled analyte into a signature ion-carrying analyte and a separated or fragmented loss group. In some embodiments the loss group can be neutral. In some embodiments the loss group can be charged. The analyte can then be quantitated based on the mass spectrum.

According to various embodiments, the signature ion-carrying analyte resulting from a second step of mass spectrometry fragmentation can be subjected to a third step of mass spectrometry fragmentation ($MS^3$). The third conditions can differ from the first conditions and differ from the second conditions and can comprise conditions that dissociate the signature ion-carrying analyte into a plurality of charged fragments. The third step of mass spectrometry fragmentation can form a second mass spectrum. In some embodiments, the analyte can be identified based on the second mass spectrum.

According to various embodiments, a molecule identification and quantitation method is provided wherein an identifiable signature ion conjugated to an analyte remains attached to the analyte after tandem mass spectrometry fragmentation ($MS^2$). Instead, only a 'mass-balance' part of a complex including the signature ion is lost as a charge neutral group under tandem mass spectrometry fragmentation. The signature ion can be used for quantitation and, upon further fragmentation, can also provide ion-signals characteristic of the analyte. In some embodiments, the ion-signals generated from a third mass spectrometry fragmentation ($MS^3$) can be compared with a known mass spectrum, for example, from a database, to provide an unambiguous identification of the analyte.

BRIEF DESCRIPTION OF THE DRAWINGS

The present teachings will be more fully understood with reference to the appended drawings, which are intended to illustrate, not limit, the present teachings.

FIGS. 2A-2E show five different mass tagging reagents that can be used according to various embodiments of the present teachings to provide simultaneous quantitation and identification of small analytes.

DETAILED DESCRIPTION

Figure 1:
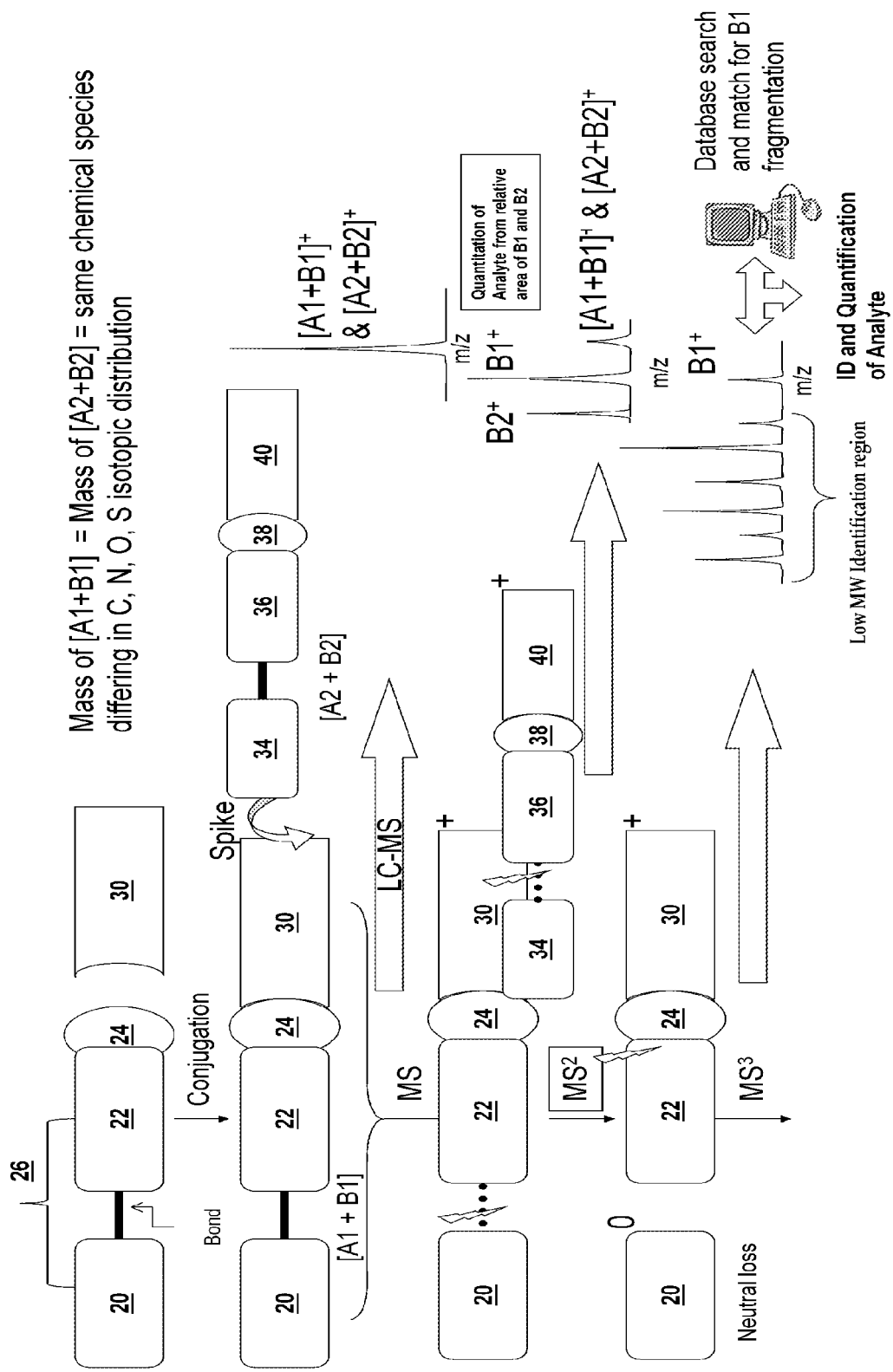
FIG. 1 is a flow diagram showing a method for the simultaneous quantitation and identification of analytes according to various embodiments of the present teachings.

According to various embodiments of the present teachings, a method of analyzing an analyte is provided that comprises both quantitating and identifying the analyte. The method can comprise covalently bonding a tag, for example, a signature ion complex, to the analyte to form a labeled analyte, for example, a bonded signature ion complex. In some embodiments, the labeled analyte can comprise a bonded analyte moiety, a signature ion moiety, and a mass balance group moiety. The method can comprise subjecting the labeled analyte to a first step of mass spectrometry fragmentation under first conditions that do not dissociate the labeled analyte. In some embodiments, the method can then comprise subjecting the labeled analyte to a second step of mass spectrometry fragmentation (MS-MS or $MS^2$) under second conditions that differ from the first conditions. The second step of mass spectrometry fragmentation can cause the formation of a mass spectrum and the second conditions can comprise conditions that dissociate the labeled analyte into a signature ion-carrying analyte and a separated or fragmented loss group. The analyte can then be quantitated based on the mass spectrum.

According to various embodiments, the signature ion-carrying analyte resulting from a second step of mass spectrometry fragmentation can be subjected to a third step of mass spectrometry fragmentation ($MS^3$). The third conditions can differ from the first conditions and differ from the second conditions and can comprise conditions that dissociate the signature ion-carrying analyte into a plurality of charged fragments. The third step of mass spectrometry fragmentation can form a second mass spectrum. In some embodiments, the analyte can be identified based on the second mass spectrum.

In some embodiments, the labeled analyte can be subjected to chromatographic separation prior to the first step of mass spectrometry fragmentation, for example, subjected to liquid chromatographic separation prior to the first step of mass spectrometry fragmentation.

In some embodiments, the method can comprise spiking the labeled analyte with a standard labeled analyte prior to the first step of mass spectrometry fragmentation. The standard labeled analyte can be of the same chemical structure and the same mass as the sample labeled analyte, but can differ in isotopic distribution. In some embodiments, the signature ion complex comprises at least two atoms selected from carbon atoms, nitrogen atoms, oxygen atoms, sulfur atoms, or a combination thereof, wherein at least one is an isotope. The standard signature ion complex in the standard labeled analyte can have the same chemical structure but a different isotopic distribution for the at least two atoms.

In some embodiments, the quantitating can be based on a first mass spectrum, and the method can comprise comparing a mass spectrum peak attributable to a labeled analyte to a mass spectrum peak attributable to a standard labeled analyte. In some embodiments, the identifying can be based on a second mass spectrum and can comprise comparing the second mass spectrum to a known mass spectrum, for example, from a known mass spectrum obtained from a look-up table, obtained from a reference source, obtained from a library, and/or obtained from a database.

According to various embodiments of the present teachings, a molecule identification and quantitation method is provided wherein a signature ion complex is conjugated to an analyte and the signature ion of the complex remains attached to the analyte after tandem mass spectrometry fragmentation (MS-MS or $MS^2$). The signature ion complex can be designed such that upon tandem mass spectrometry fragmentation, a mass-balance part of the signature ion complex is lost as a charge neutral group but the signature ion remains attached to the analyte. In some embodiments, the signature ion can be fragmented from the analyte after a third step or stage of mass spectrometry fragmentation ($MS^3$). The signature ion can be used for quantitation, and upon further fragmentation, can also provide ion signals characteristic of the analyte. The characteristic ion signals are used according to various embodiments to identify the analyte. In some embodiments, the ion-signals generated from a third mass spectrometry fragmentation ($MS^3$) can be compared with a known mass spectrum, for example, from a reference or from a database, to provide an unambiguous identification of the analyte.

FIG. 1 is a schematic diagram showing a method of simultaneously quantitating and identify analytes, according to various embodiments of the present teachings. As shown at the top left of the schematic diagram, a mass balance group 20 is bonded to a mass recognition group 22 having a reactive end 24, to form a complex 26. Mass recognition group 22 is configured to form an identifiable signature ion but only after three steps of mass spectrometric fragmentation ($MS^3$), as discussed below. Complex 26 is conjugated to an analyte 30 through a reaction at reactive end 24, and the result is spiked with a standard complex 32. Thereafter, the resulting mixture is subject to liquid chromatography to separate the various components, and the separated components are subject to a first step of mass spectrometry (MS).

As shown in FIG. 1, the signature ion does not detach itself from analyte 30 after a second step of mass spectrometry ($MS^2$) fragmentation. Instead, only a mass-balance part of the molecule is lost, for example, as a charge neutral group. This remaining signature ion can be used for quantitation and upon further fragmentation provides ion signals, characteristic of analyte 30. The ion signals detected can be compared with a database to provide an unambiguous identification of analyte 30, as further depicted in FIG. 1.

Figure 3:
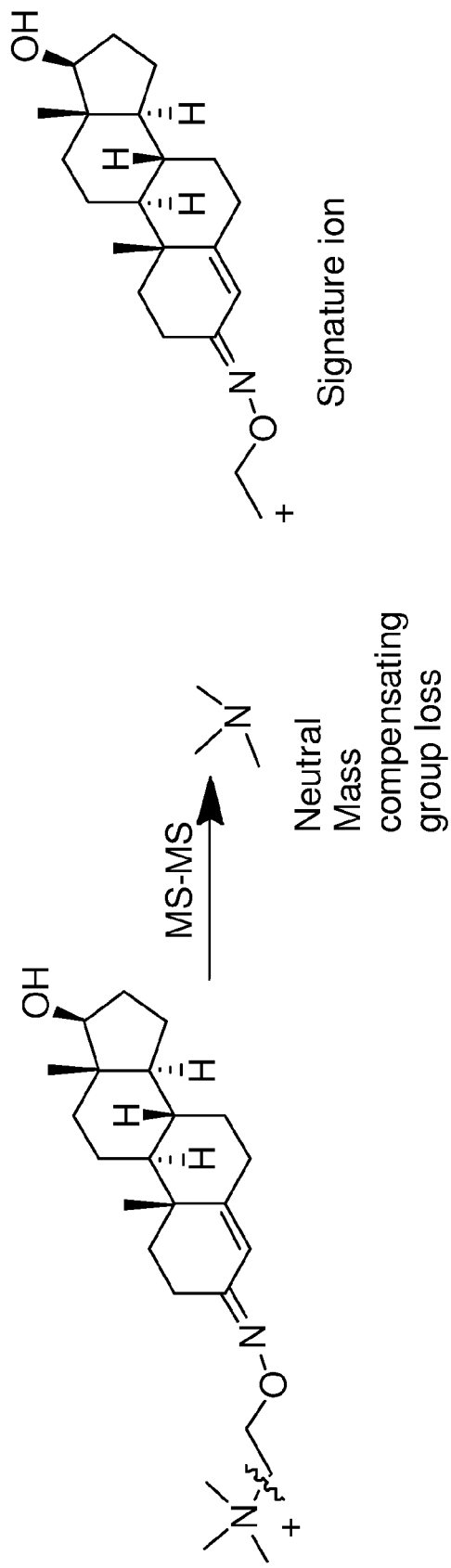
FIG. 3 is a reaction scheme showing the generation of a signature ion-containing analyte in an MS-MS mode, according to various embodiments of the present teachings.

According to various embodiments, examples of mass tagging reagents which can be used to provide the simultaneous quantitation and identification of small molecules, are shown in FIGS. 2A-2E. The typical $MS^2$ fragmentation pattern for the exemplary mass tagging reagent shown in FIG. 2A, is demonstrated in FIG. 3. As shown in FIG. 3, a reaction with the mass tagging reagent undergoing MS-MS fragmentation generates a signature ion containing the analyte and generates a neutral mass compensating group.

Figure 4:
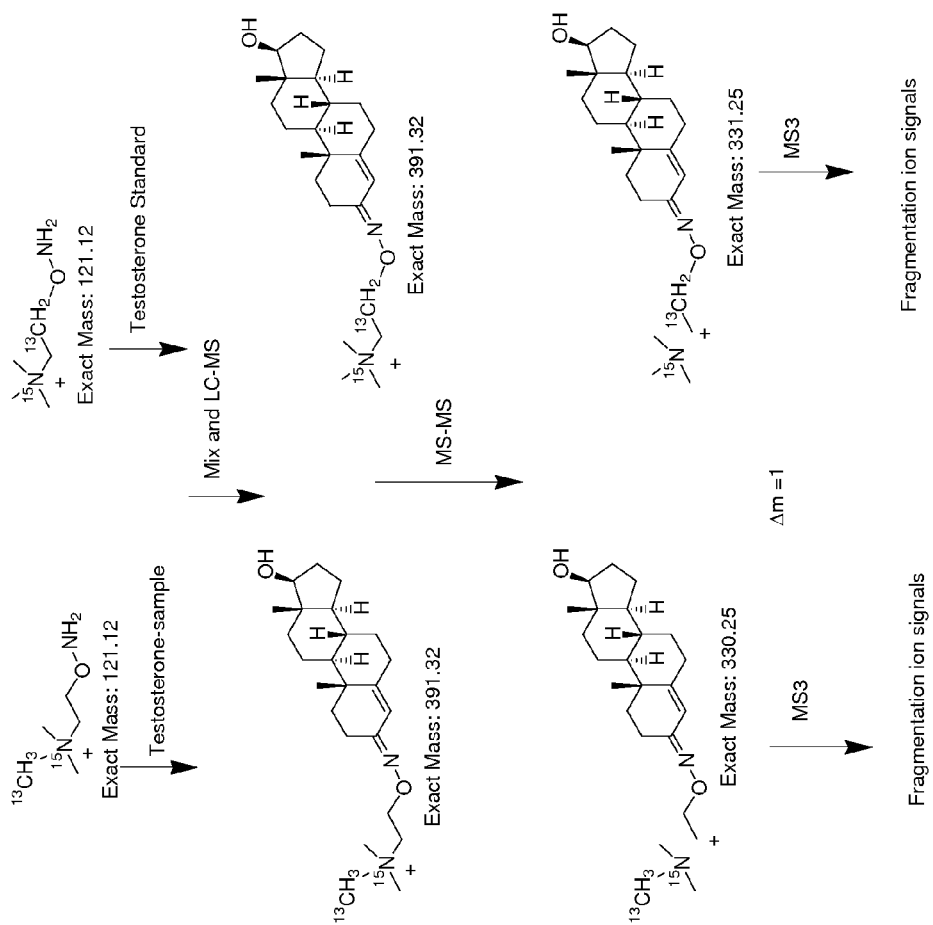
FIG. 4 is a two-plex reaction scheme for a two-plex reagent configuration useful to detect and quantitate the steroid testosterone, according to various embodiments of the present teachings.

According to various embodiments, the present teachings provide methods that utilize a two-plex reagent configuration for the identification and quantitation of small molecules. As shown in FIG. 4, a two-plex reagent configuration is provided for the steroid testosterone. As shown in FIG. 4, a testosterone-containing sample is labeled with a first mass tagging reagent and a testosterone-containing standard is labeled with a different mass tagging reagent, wherein both tagging reagents have the same exact mass, particularly, 121.12 atomic mass units (amu). After the respective tagging, the testosterone-containing sample and the testosterone-containing standard are mixed and LC-MS is performed followed by MS-MS ($MS^2$). After $MS^3$ fragmentation, ion signals can be compared with a reference or with a database to identify the sample. According to various embodiments, methods of synthesizing mass tagging reagents are provided and are exemplified in FIG. 5.

Figure 5:
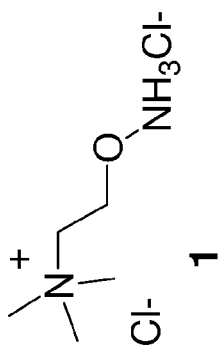
FIG. 5 shows a reaction scheme for the synthesis of the signature ion-containing reagent tri-methyl ammonium ethylene hydroxyl amine HCl, according to various embodiments of the present teachings.
Figure 5:
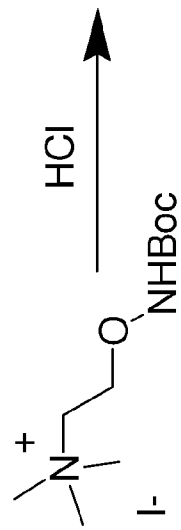
Figure 5:

FIG. 5 shows the synthesis of tri-methyl ammonium ethylene hydroxyl amine hydrochloride. The tagging reagent can be used to derivatize testosterone and estrone, which can then be subjected to quantitation and identification according to various embodiments. After identification, mass spectroscopic data can be collected, as shown in FIG. 6, which illustrates embodiments wherein distinct identification ion signals are provided for two different analytes.

Figure 6:
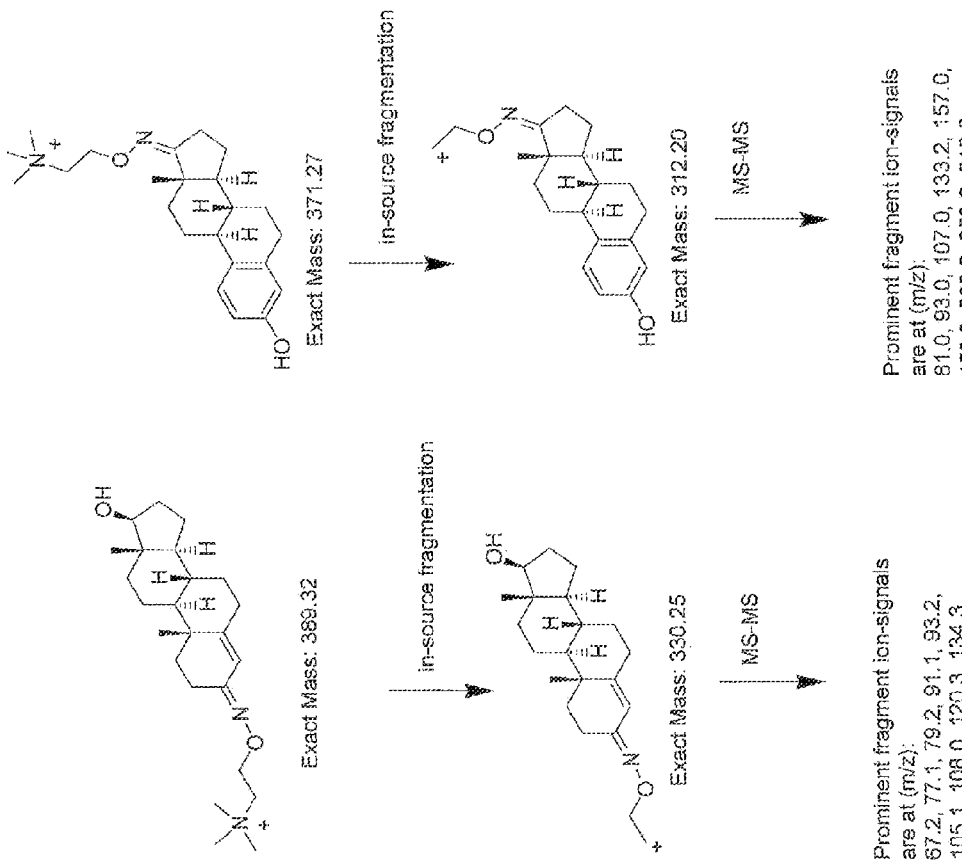
FIG. 6 shows a reaction scheme useful for generating the distinct identification ion-signals for two different analytes, according to various embodiments of the present teachings.

FIG. 6 shows the distinct identification ion signals for the two different analytes. In an exemplary embodiment, the MS-MS step of the method to fragment the signature ion was conducted using an API 3200 DP value set to "high" so that in-source fragmentation was sufficient to generate the signature ion.

According to yet other embodiments of the present teachings, a kit is provided that comprises at least one tag in the form of a signature ion complex as described herein, and a set of instructions for carrying out a method as described herein. The kit can also comprise a standard labeled analyte or standard signature ion complex, wherein the standard signature ion complex is of the same chemical structure and mass as the signature ion complex but differs from the signature ion complex in isotopic distribution. The instructions can comprise instructions for quantitating the analyte by comparing a mass spectrum peak attributable to a bonded signature ion complex to a mass spectrum peak attributable to a standard labeled analyte or bonded signature ion complex. The instructions can comprise instructions for identifying the analyte by comparing a mass spectrum to a mass spectrum obtained from, for example, from a known mass spectrum obtained from a look-up table, from a reference source, from a library, from a database and/or from a link to a database. In some embodiments, the kit can further comprise a plurality of different standard signature ion complexes, wherein each standard signature ion complex is of the same chemical structure and mass as the signature ion complex but differs in isotopic distribution.

In some embodiments, the kit can comprise enzyme digestion components including buffers and enzymes, other buffers, and optionally other reagents and/or components. In some embodiments, the kit can comprise, for example, a homogeneous assay such that the user need only add a sample. In some embodiments, the kit can comprise calibration or normalization reagents or standards. Information pertaining to instrument settings that can or should be used to perform an assay can also be included in the kit. Information pertaining to sample preparation, operating conditions, volumetric amounts, temperature settings, and the like, can be included with the kit. The kit can comprise different transition values and/or suggested settings, useful to make comparative measurements between a sample and one or more control reagents. The kit can include instructions to measure specific pairs of transition values, for example, the Q1/Q3 transition pair, or the values of one or more different transition pairs.

In some embodiments, the kit can be packaged in a hermetically sealed container containing one or more regent vessels and appropriate instructions. An electronic medium can be included in the kit, having stored thereon electronic information pertaining to one or more assays, measurement values, transition pairs, operating instructions, software for carrying out operations, a combination thereof, or the like. In some embodiments, the kit can comprise a pointer indicating where information, for example, a mass spectrum or mass spectrum data, can be found. The pointer can comprise, for example, a web address, a user name, a password, a combination thereof, and the like.

The present teachings will now be illustrated with reference to the following examples. While testosterone and estrone are exemplified as analytes, it is to be understood that any of a variety of analytes can be quantized and identified according to the present teachings, for example, including other steroids, aldehydes, ketones, combinations thereof, and the like.

EXAMPLES

In two exemplary embodiments, a signature ion complex 1 (FIG. 5) was synthesized in accordance with the reaction scheme shown in FIG. 5. Testosterone and estrone were then each derivatized with signature ion complex 1. FIG. 6 shows the next step in the method wherein the derivatized testosterone and estrone, after being subjected to liquid chromatographic separation, were subject to mass spectrometric fragmentation from which mass spectroscopic data was collected. As can be seen in FIG. 6, two different distinct sets of ID ion-signals were generated for the two, respective, different analytes. In some embodiments, such as embodiments using a fully-integrated triple quadrupole mass spectrometer such as the API 3200 from Applied Biosystems, Foster City, Calif., the DP value was set to high so that in-source fragmentation generated the signature ion and MS-MS ($MS^2$) of the signature ion was enabled. Data generated from the method is shown in FIGS. 7-9A and 10-12.

Figure 7:
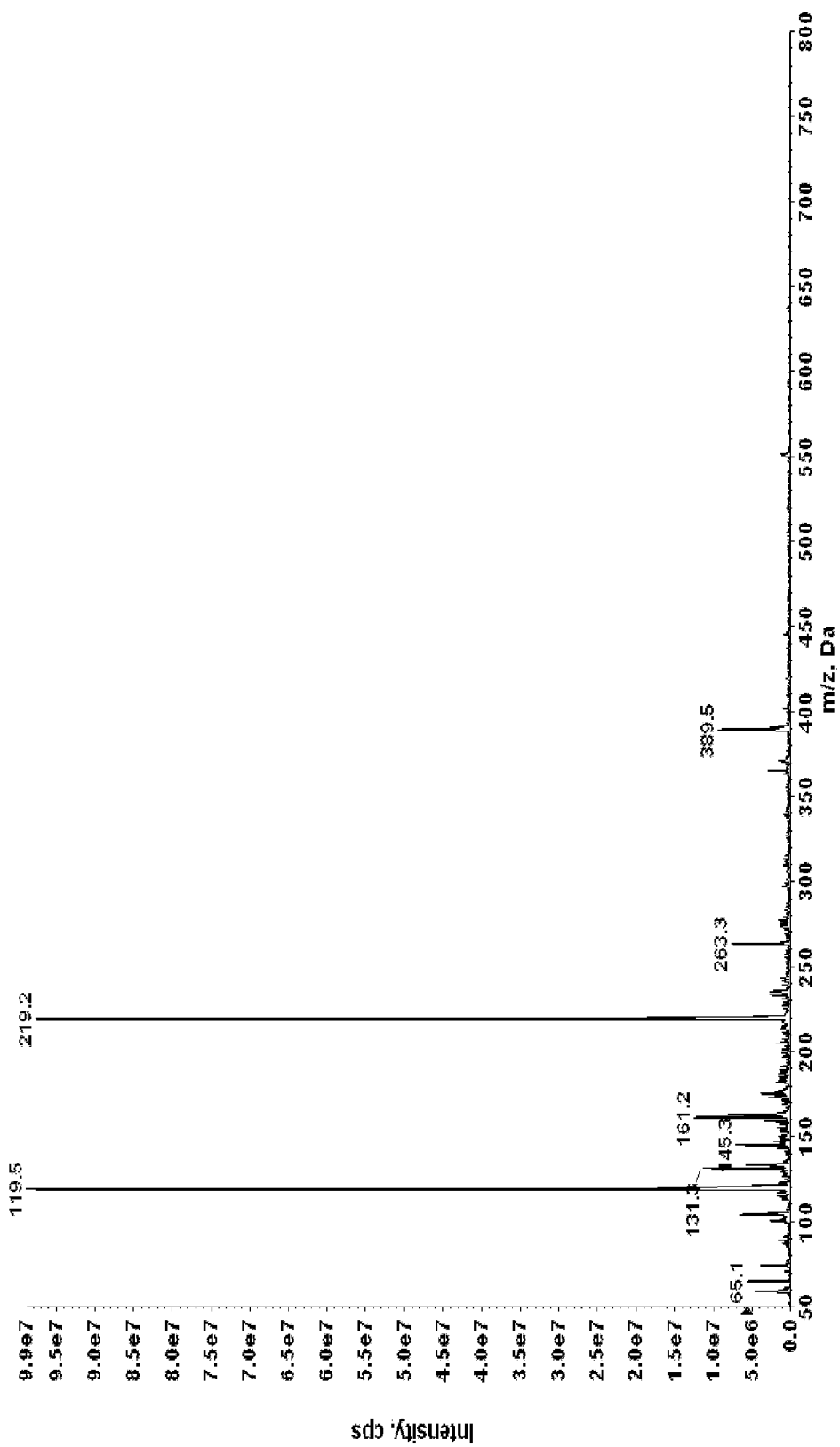
FIG. 7 is a mass spectrogram of various fragments of testosterone, generated from a first mass spectrometric separation, according to various embodiments of the present teachings.
Figure 8:
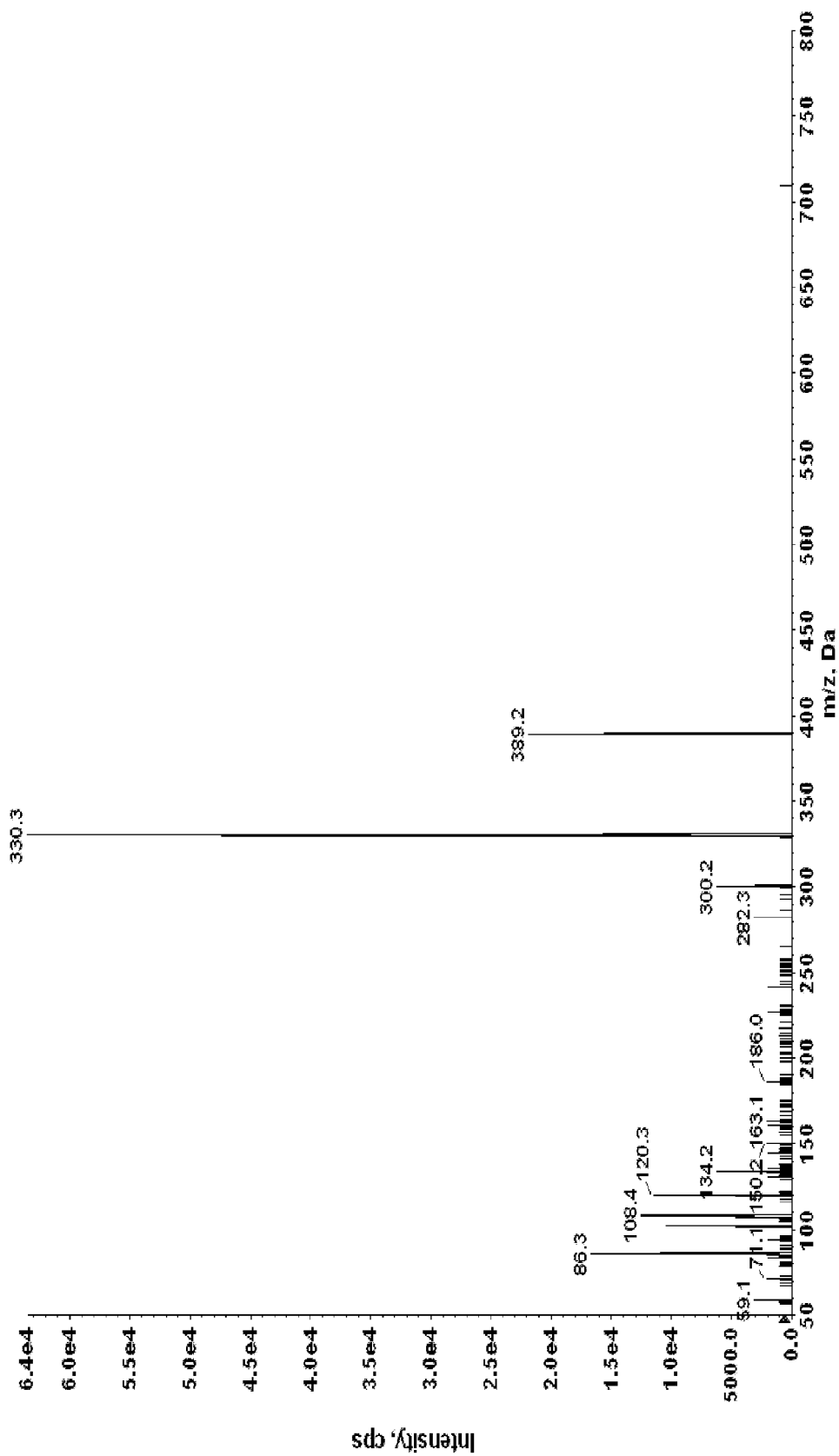
FIG. 8 is a mass spectrogram of various fragments of testosterone generated from two mass spectrometric separations (MS-MS, or tandem mass spectrometry), according to various embodiments of the present teachings.
Figure 9A:
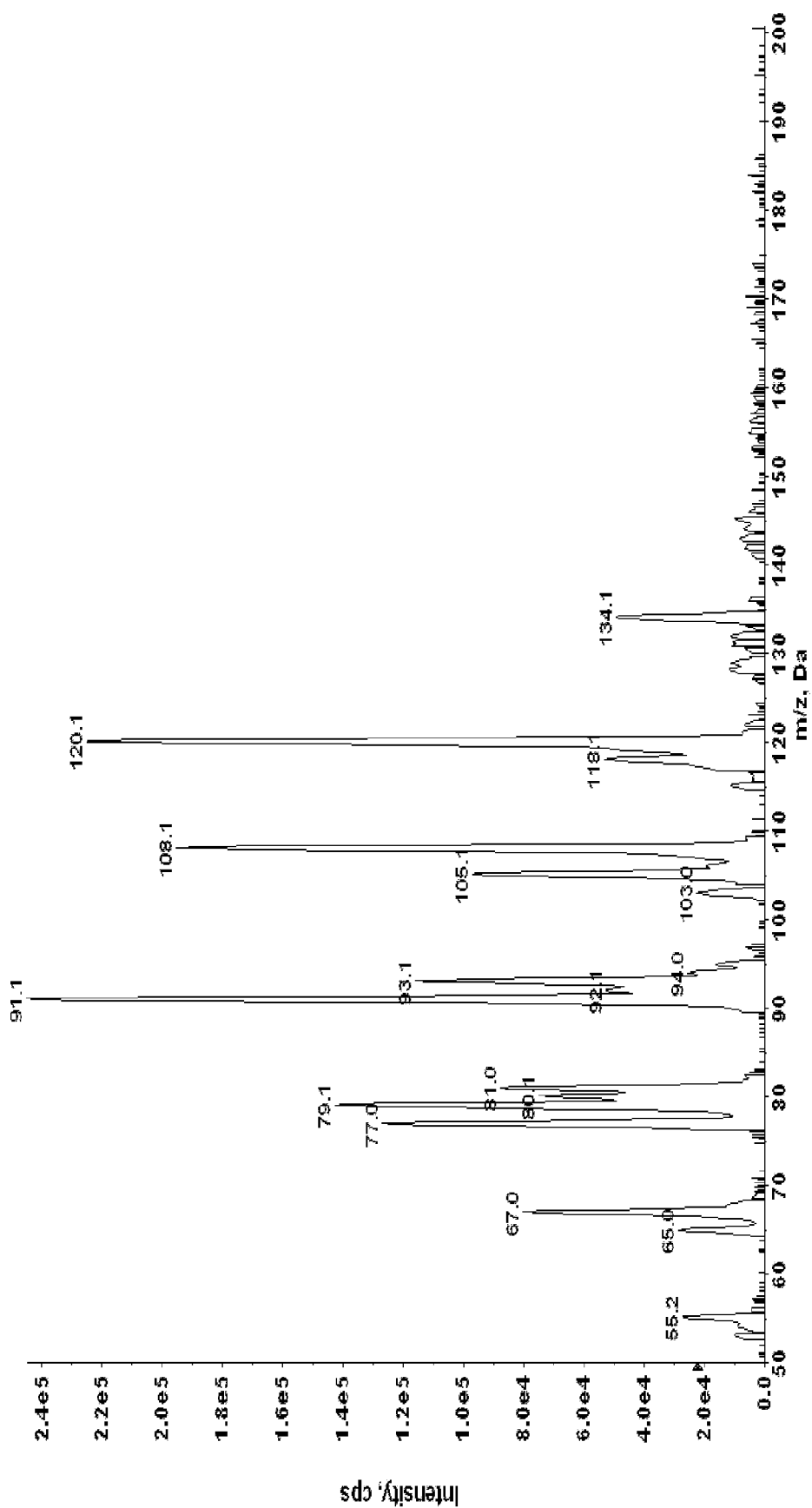
FIG. 9A is a mass spectrogram of various fragments of testosterone generated from three mass spectrometric separations ($MS^3$), and showing a signature ion, according to various embodiments of the present teachings.

FIG. 7 is a mass spectrogram of various fragments of testosterone, generated from a first mass spectrometric separation. FIG. 8 is a mass spectrogram of various fragments of testosterone generated from a second mass spectrometric separation using $MS^2$ (MS-MS, or tandem mass spectrometry). FIG. 9A is a mass spectrogram of various fragments of testosterone generated from a third step of mass spectrometric separation ($MS^3$), and shows a peak corresponding to the signature ion.

Figure 9B:
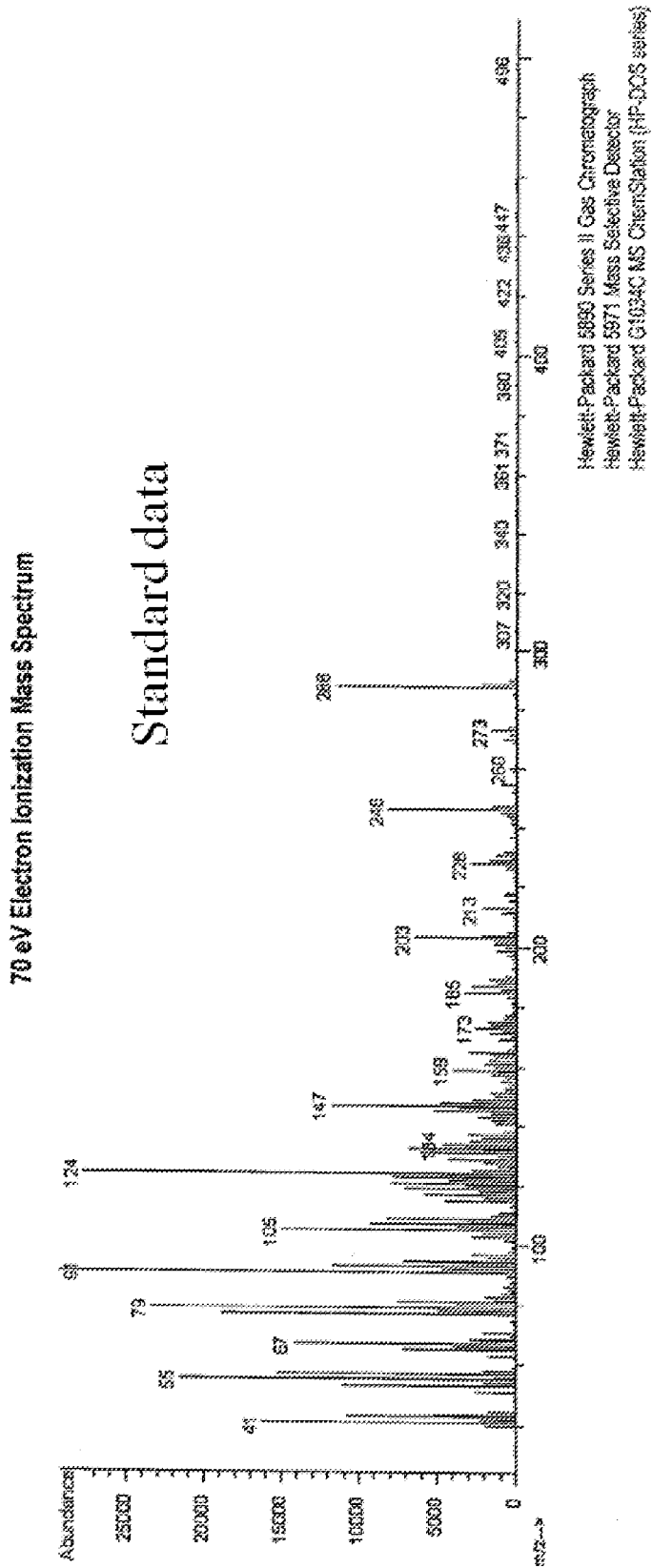
FIG. 9B is a mass spectrogram of various fragments of testosterone, taken from a data source, which in this case is an excerpt from a Product Information sheet for Testosterone Steroid in methanol solution, obtained from Sigma-Aldrich, St. Louis, Mo.

In accordance with various embodiments, the signature ions were compared to data available from known mass spectra. For example, the testosterone signature ion from $MS^3$ according to the present teachings, shown in FIG. 9A, was compared to standard data available from a mass spectrum of testosterone steroid. Although a database can be used, the data generated and shown in FIG. 9A was compared to a mass spectrum and obtained from Sigma-Aldrich, St. Louis, Mo., which is shown in FIG. 9B. The mass spectrum of FIG. 9B is an excerpt taken from the Sigma-Aldrich Product Information sheet for product number T 5411 (Testosterone Steroid). FIG. 9B is a mass spectrogram of various fragments of testosterone from a sample in methanol solution.

Figure 10:
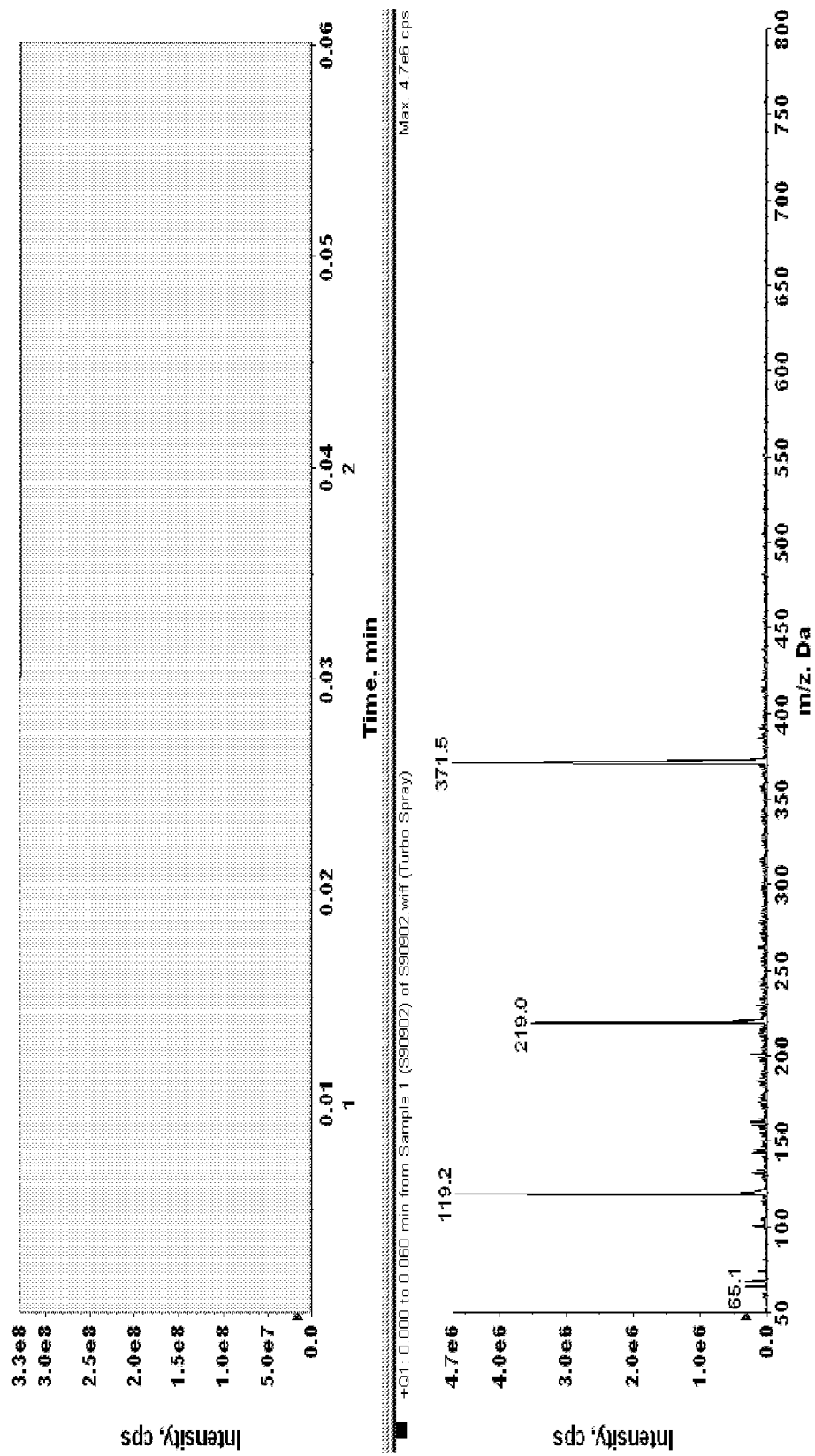
FIG. 10 is a mass spectrogram of various fragments of estrone, generated from a first mass spectrometric separation, according to various embodiments of the present teachings.
Figure 11:
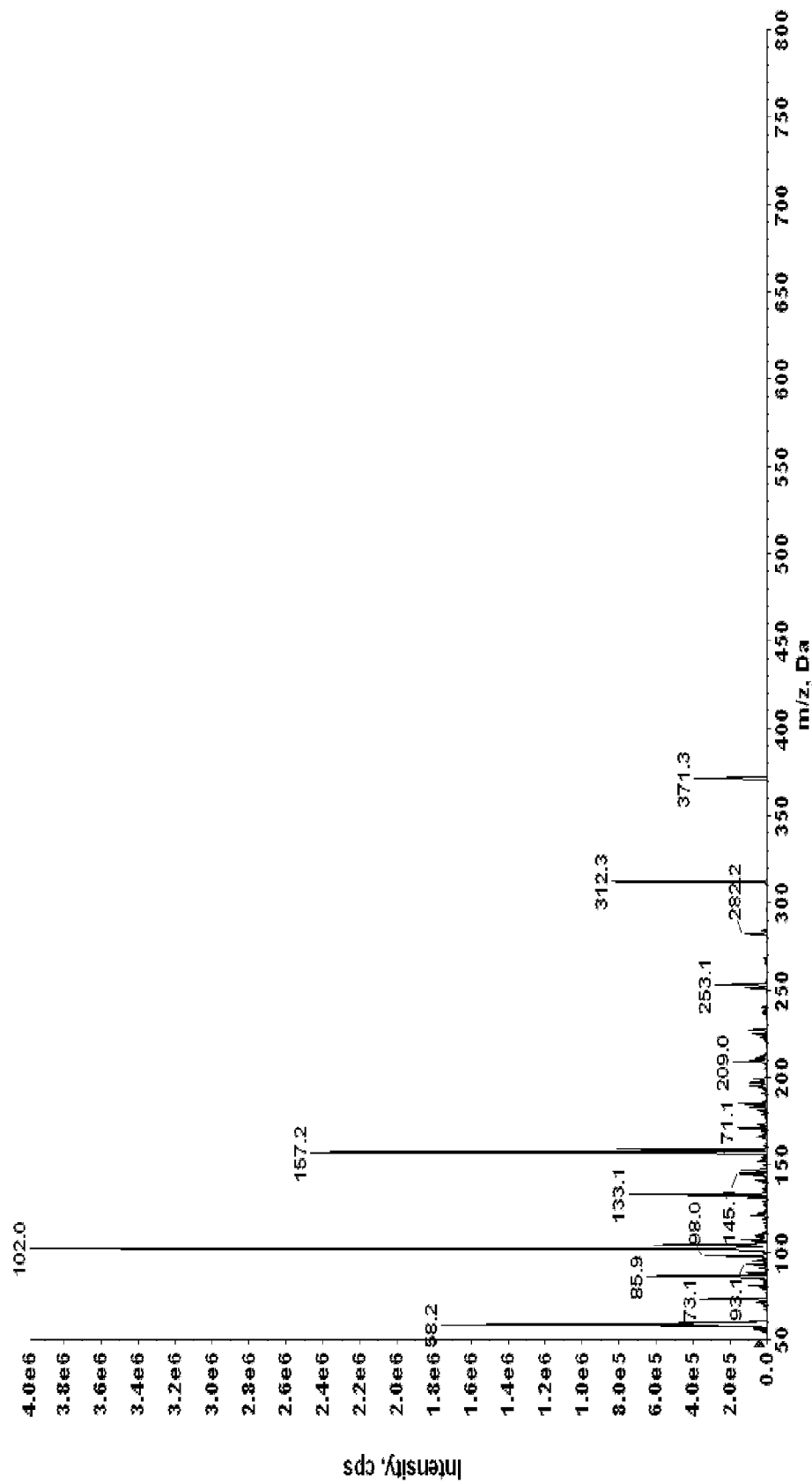
FIG. 11 is a mass spectrogram of various fragments of estrone generated from two mass spectrometric separations (MS-MS, or tandem mass spectrometry), according to various embodiments of the present teachings.
Figure 12:
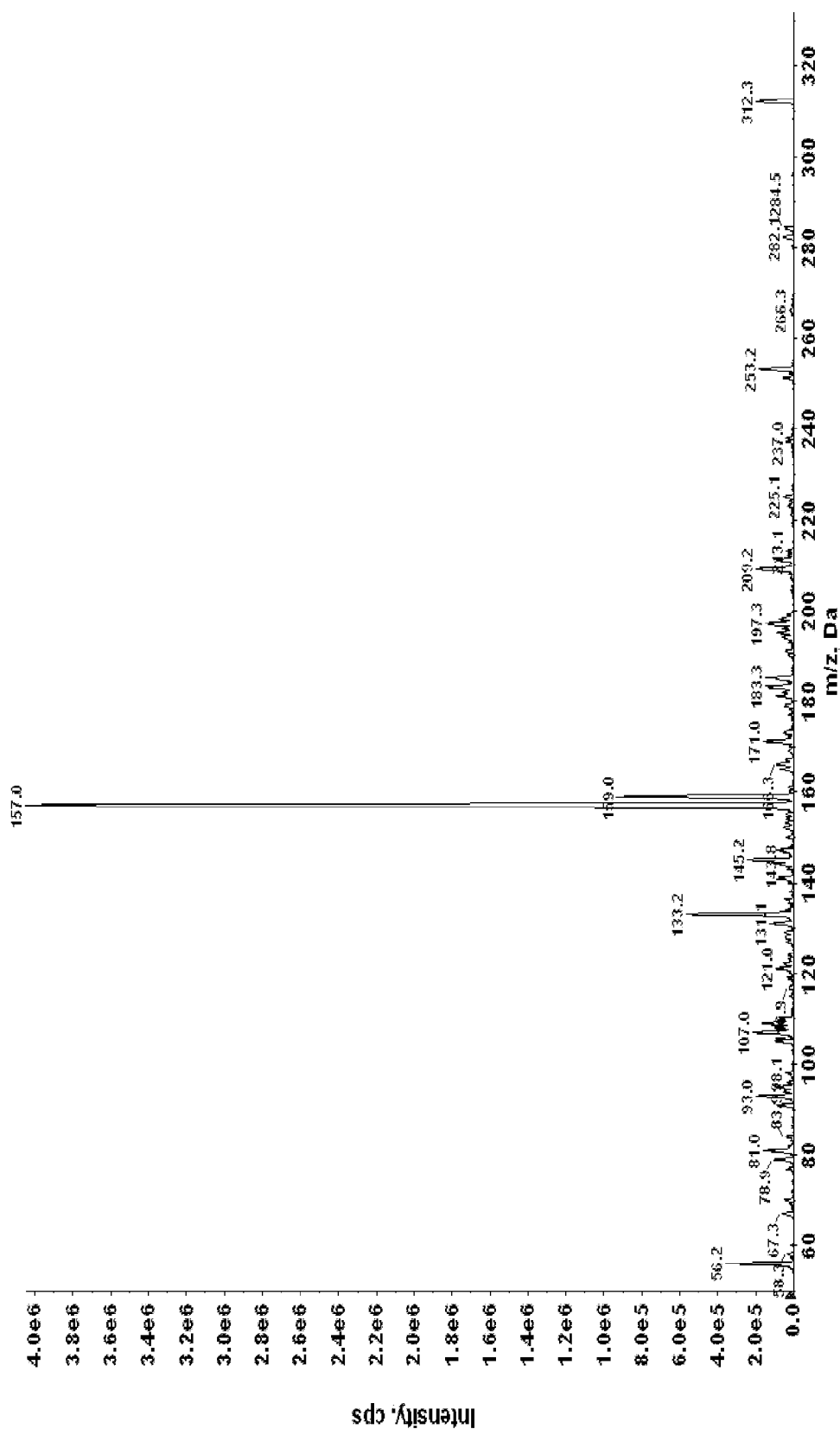
FIG. 12 is a mass spectrogram of various fragments of estrone generated from three mass spectrometric separations ($MS^3$), and showing a signature ion, according to various embodiments of the present teachings.

FIG. 10 is a mass spectrogram of various fragments of estrone, generated from a first mass spectrometric separation, FIG. 11 is a mass spectrogram of various fragments of estrone generated from a second mass spectrometric separation, and FIG. 12 is a mass spectrogram of various fragments of estrone generated from a third mass spectrometric separation ($MS^3$). FIG. 12 shows the signature ion and the mass spectrum was compared to a mass spectrum taken from a database.

Other embodiments of the present teachings will be apparent to those skilled in the art from consideration of the present specification and practice of the present teachings disclosed herein. It is intended that the present specification and examples be considered exemplary only.

What is claimed:

1. A method of analyzing an analyte, comprising:
   covalently bonding a mass tag to an analyte to form a labeled analyte;
   subjecting the labeled analyte to a first step of mass spectrometry fragmentation under first conditions that do not dissociate the labeled analyte;
   subjecting the labeled analyte to a second step of mass spectrometry fragmentation under second conditions that differ from the first conditions, the second step of mass spectrometry fragmentation forming a mass spectrum and the second conditions comprising conditions that dissociate the labeled analyte into a charged, signature ion-carrying analyte and a separated neutral loss group;
   quantitating the analyte based on the mass spectrum;

subjecting the charged, signature ion-carrying analyte to a third step of mass spectrometry fragmentation under third conditions that differ from the first conditions and differ from the second conditions, the third step of mass spectrometry fragmentation forming a second mass spectrum and the third conditions comprising conditions that dissociate the charged, signature ion-carrying analyte into a plurality of charged fragments; and identifying the analyte based on the second mass spectrum.

2. The method of claim 1, further comprising subjecting the labeled analyte to chromatographic separation prior to the first step of mass spectrometry fragmentation.

3. The method of claim 1, further comprising subjecting the labeled analyte to liquid chromatographic separation prior to the first step of mass spectrometry fragmentation.

4. The method of claim 1, further comprising spiking the labeled analyte with a standard labeled analyte prior to the first step of mass spectrometry fragmentation, wherein the standard labeled analyte is of the same chemical structure and mass as the labeled analyte but differs in isotopic distribution.

5. The method of claim 4, wherein the labeled analyte comprises at least two atoms selected from carbon atoms, nitrogen atoms, oxygen atoms, sulfur atoms, or a combination thereof.

6. The method of claim 4, wherein the quantitating the analyte based on the mass spectrum comprises comparing a mass spectrum peak attributable to the labeled analyte to a mass spectrum peak attributable to the standard labeled analyte.

7. The method of claim 1, wherein the identifying the analyte based on the second mass spectrum comprises comparing the second mass spectrum to a known mass spectrum.

8. The method of claim 7, wherein the comparing the second mass spectrum to a known mass spectrum comprises looking up a known mass spectrum from a database.

9. The method of claim 1, wherein the mass tag comprises a complex selected from the group consisting of the complex of FIG. 2A, the complex of FIG. 2B, the complex of FIG. 2C, the complex of FIG. 2D, the complex of FIG. 2E.

10. The method of claim 1, wherein the mass tag comprises tri-methyl ammonium ethylene hydroxyl amine HCl.

11. The method of claim 1, wherein the analyte comprises testosterone.

12. The method of claim 1, wherein the analyte comprises estrone.

13. The method of claim 1, wherein the analyte comprises an aldehyde, a ketone, or a combination thereof.

* * * * *